United States Patent [19]
Koros et al.

[11] Patent Number: 5,352,235
[45] Date of Patent: Oct. 4, 1994

[54] LAPAROSCOPIC GRASPER AND CUTTER

[76] Inventors: Tibor Koros; Gabriel Koros, both of 610 Flinn Ave., Moorpark, Calif. 93021

[21] Appl. No.: 967,086

[22] Filed: Oct. 27, 1992

Related U.S. Application Data

[63] Continuation-in-part of Ser. No. 853,307, Mar. 16, 1992.

[51] Int. Cl.$^5$ .............................................. A61B 17/32
[52] U.S. Cl. ..................................... 606/174; 606/170
[58] Field of Search .................... 606/51, 52, 83, 167, 606/170, 174, 205–211, 41; 128/3–6, 751–755; 81/300, 304, 313–319, 342

[56] References Cited

U.S. PATENT DOCUMENTS

| | | | |
|---|---|---|---|
| 3,964,468 | 6/1976 | Schulz | 128/751 |
| 4,427,014 | 1/1984 | Bel et al. | 128/751 |
| 4,819,633 | 4/1989 | Bauer et al. | 606/52 |
| 5,209,747 | 5/1993 | Knoepfler | 606/52 |
| 5,211,655 | 5/1993 | Hasson | 606/205 |

*Primary Examiner*—Stephen C. Pellegrino
*Assistant Examiner*—William Lewis
*Attorney, Agent, or Firm*—Jessup & Slehofer

[57] ABSTRACT

A laparoscope instrument is formed by a shaft combination, a pair of squeeze handles, a socket, a stationary barrel, a movable barrel, and a clutch. The socket is attached to the proximal handle. The shaft combination has an outer hollow shaft and an inner shaft. The inner shaft has a pair of cutting tips or grippers at the distal operating end. The other end of the inner shaft has an anchor point for engaging with the socket at the other end of the instrument. The socket holds the end of the inner shaft and causes the shaft to reciprocate slightly in response to the surgeon closing or opening the pair of handles. The cutting tips close or open in response to the squeezing action by the surgeon. The socket has a quick-release button to allow the inner shaft with the cutting tips to be quickly removed from the instrument, and replaced with another shaft and cutting tips. The instrument does not have to be disassembled. The clutch allows the surgeon to quickly change the angular orientation of the cutting tips during the operation. A thumb wheel forming part of the clutch can be easily turned to make the adjustment. The instrument can have a plug for connecting to an electric cord to allow the instrument to be used in cauterization techniques. The outer surfaces are covered with a vinyl insulation to prevent electrical shock.

24 Claims, 8 Drawing Sheets

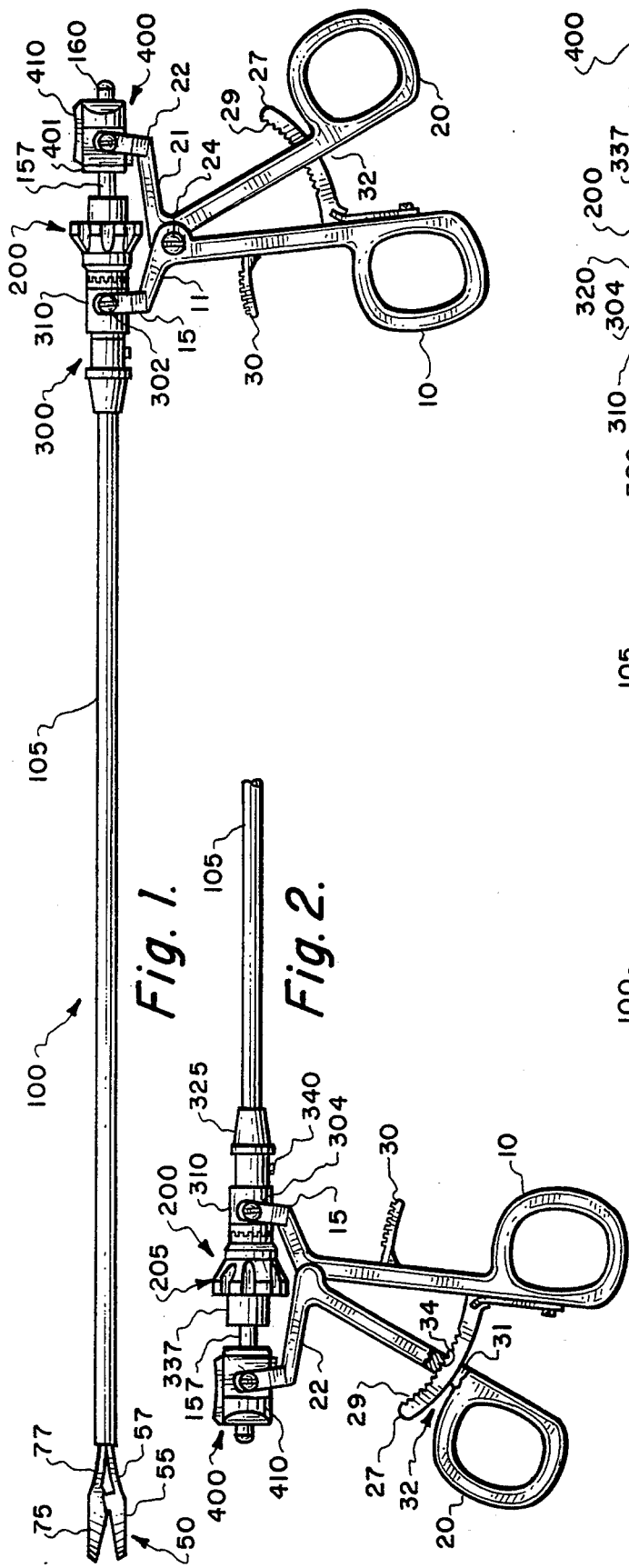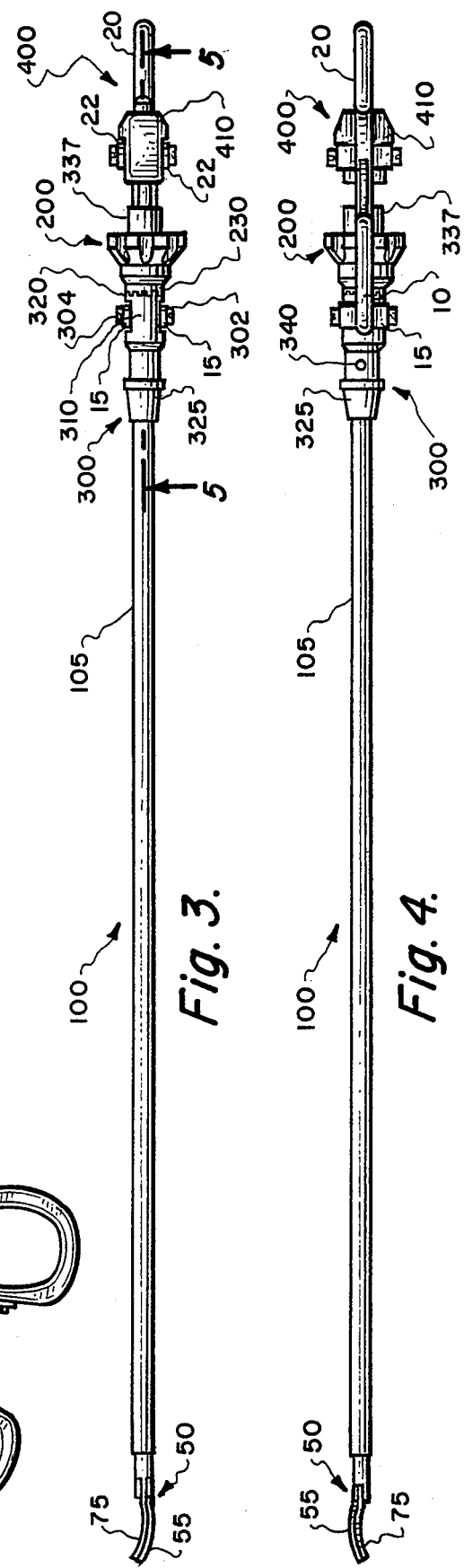

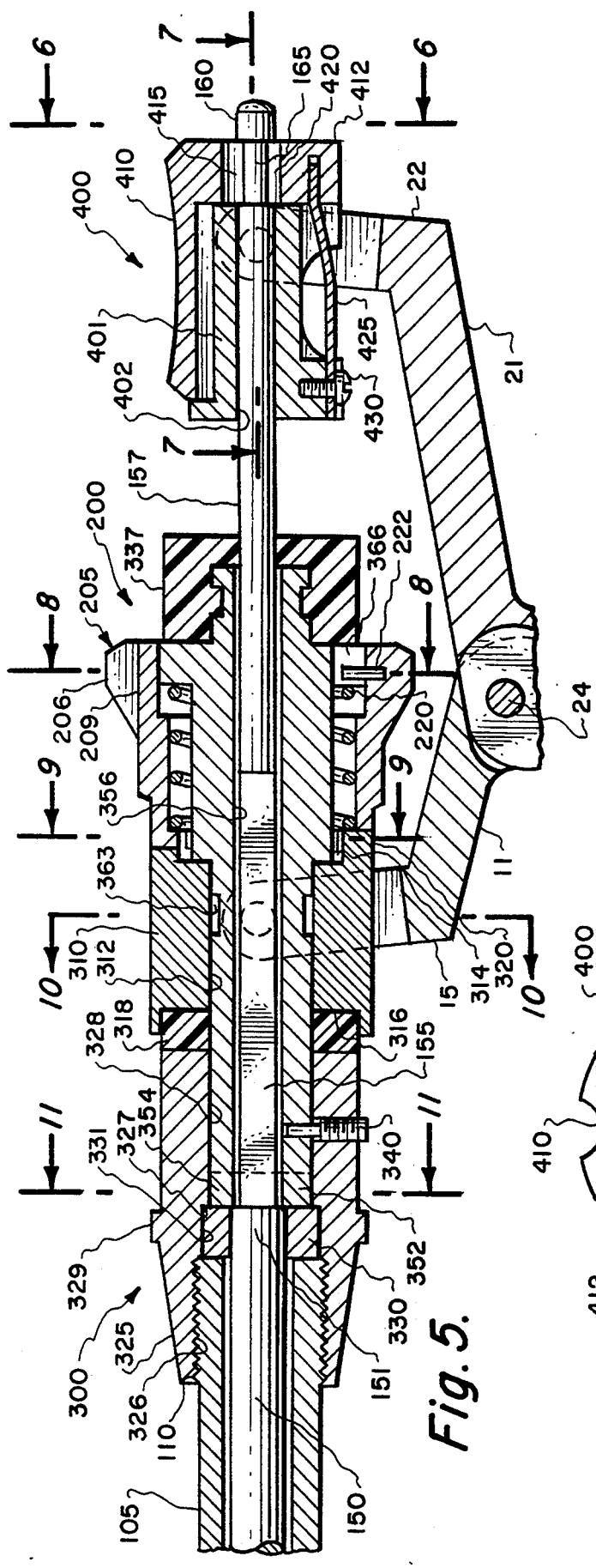
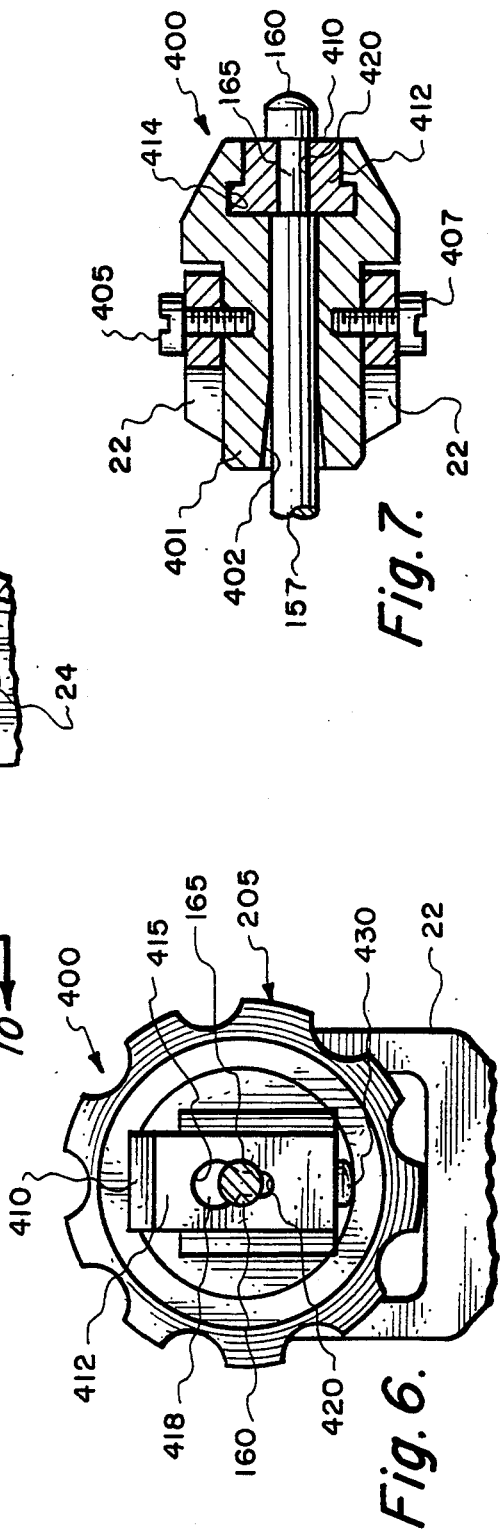
Fig. 5.
Fig. 6.
Fig. 7.

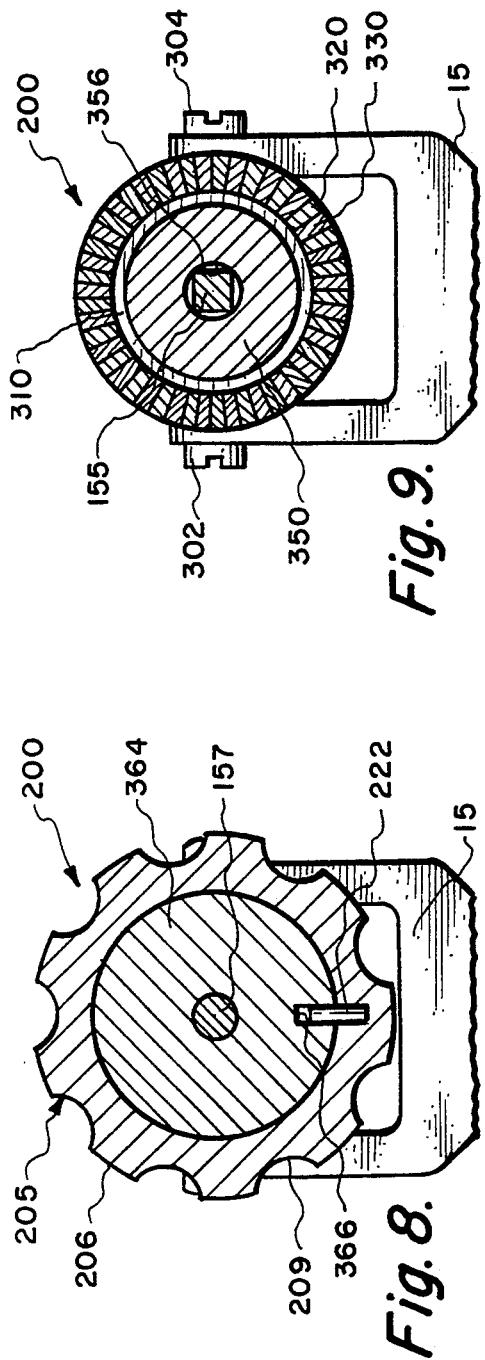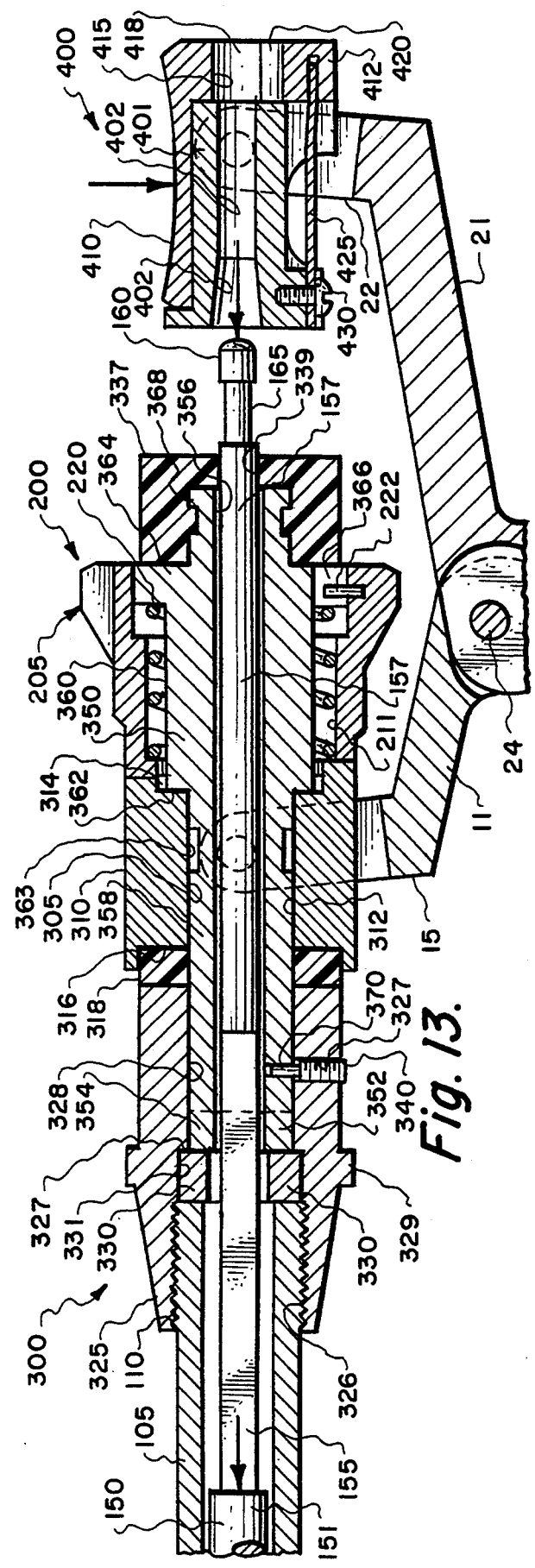

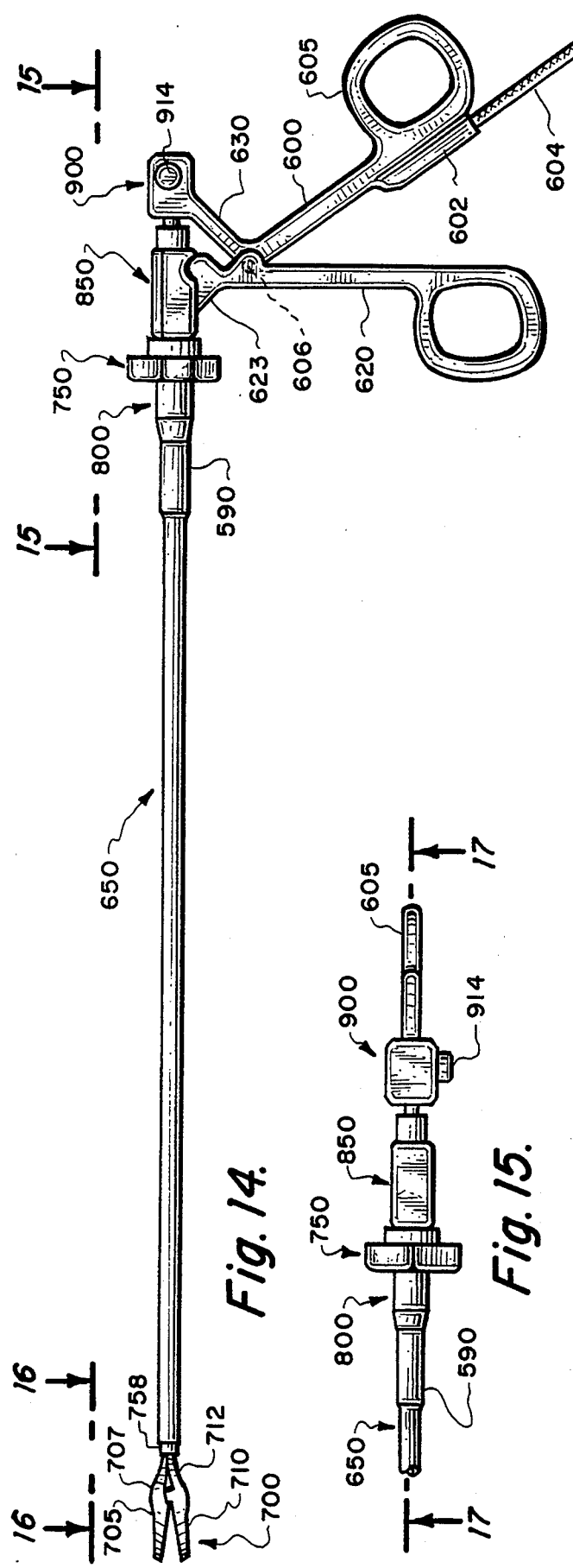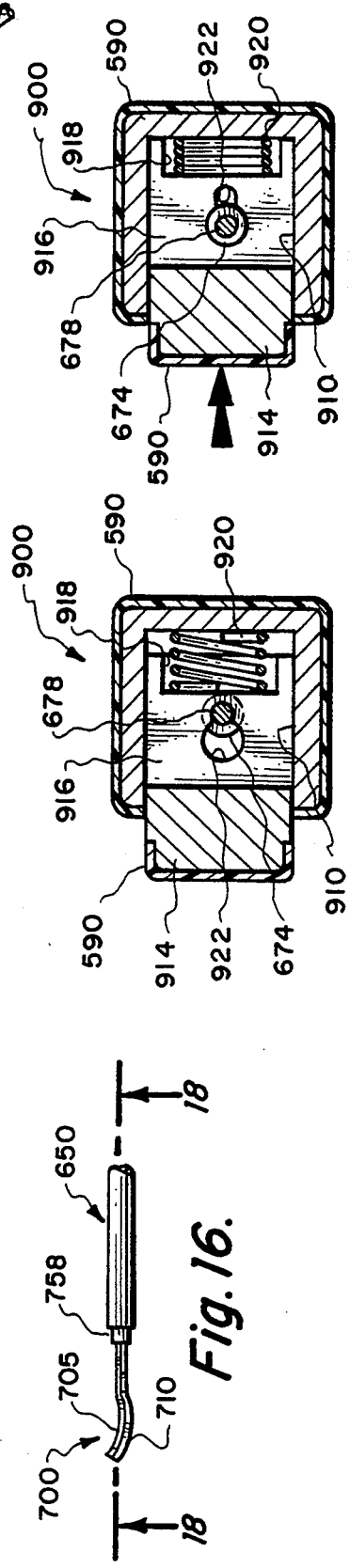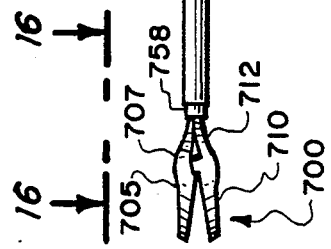

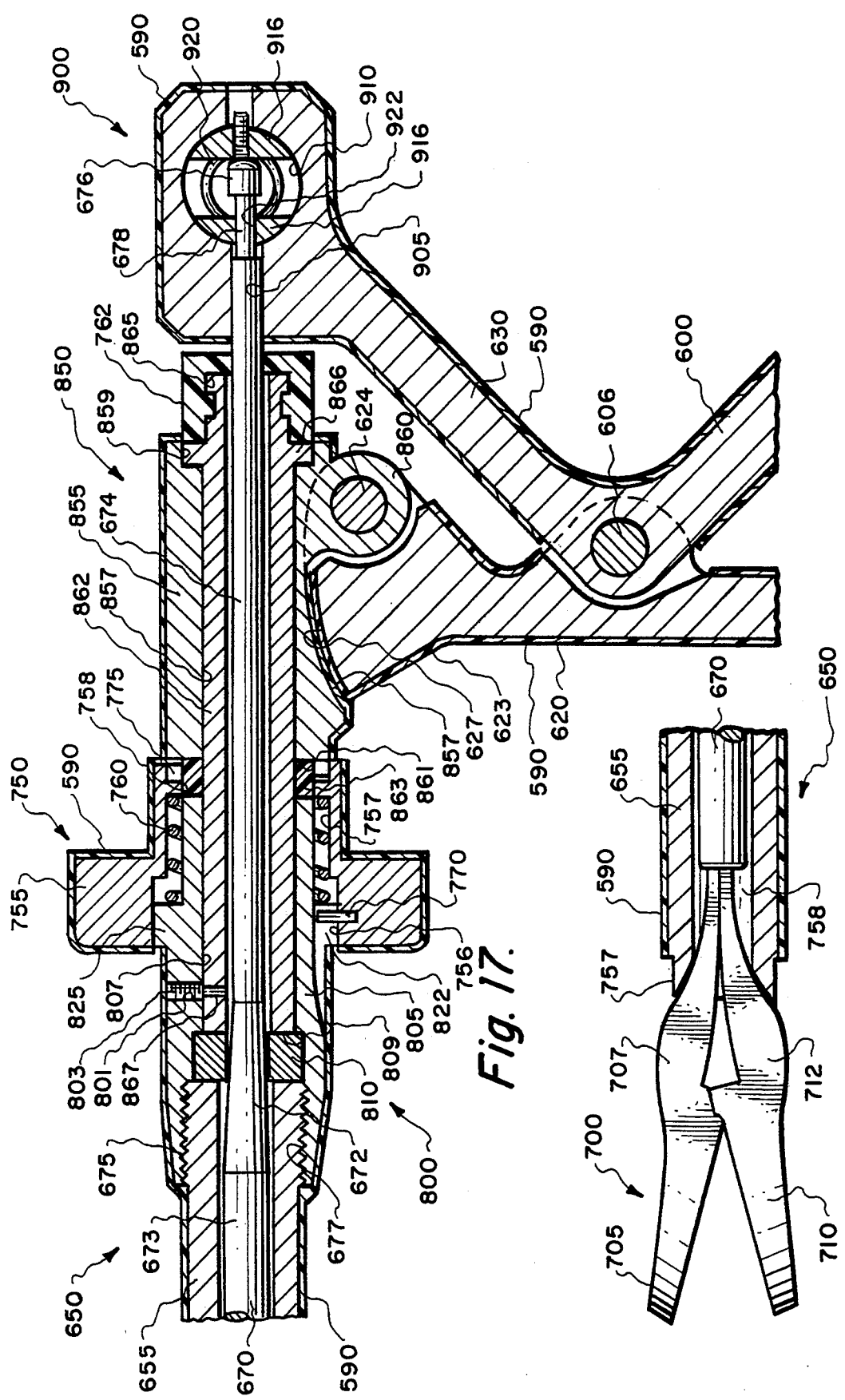

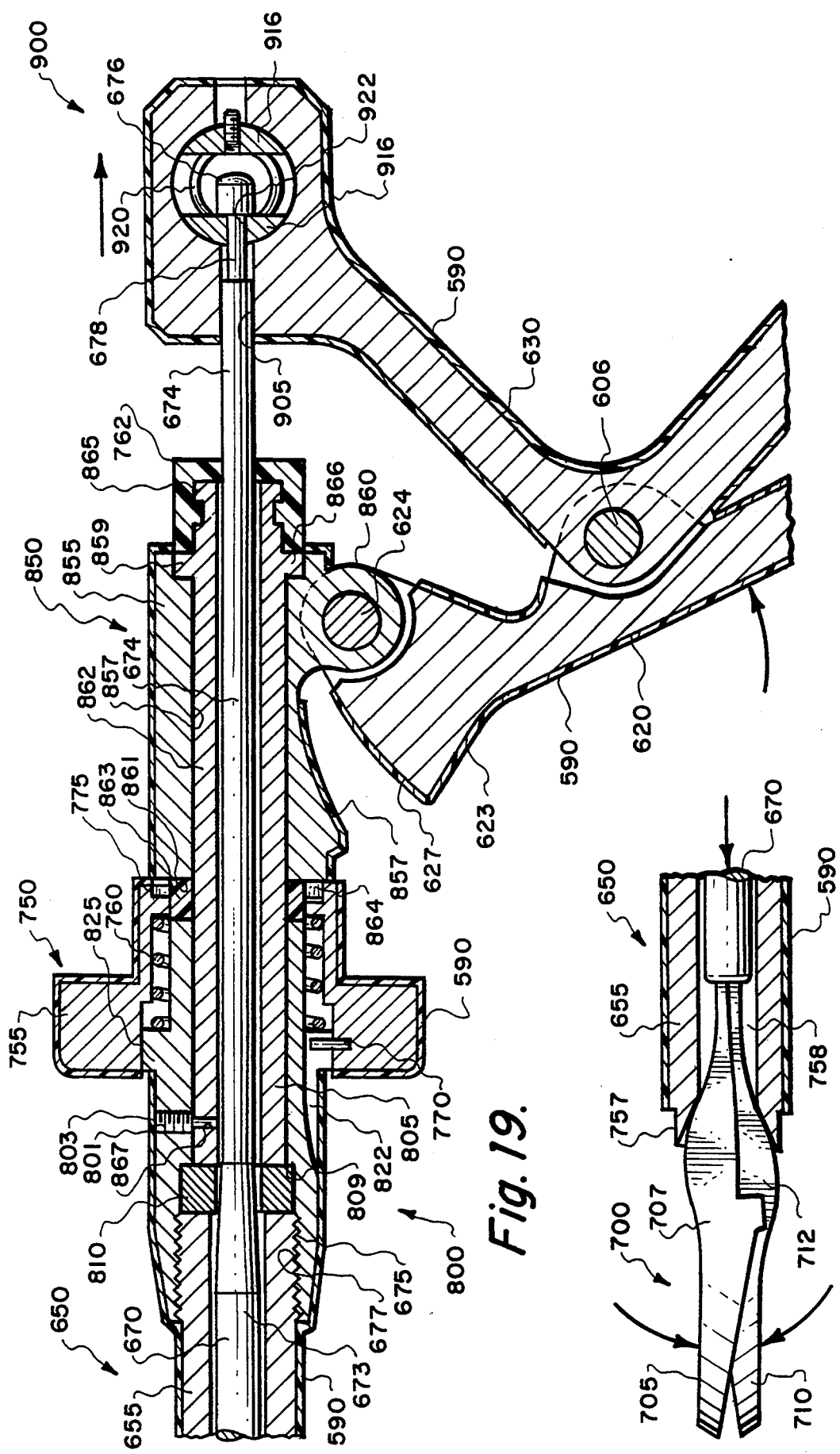

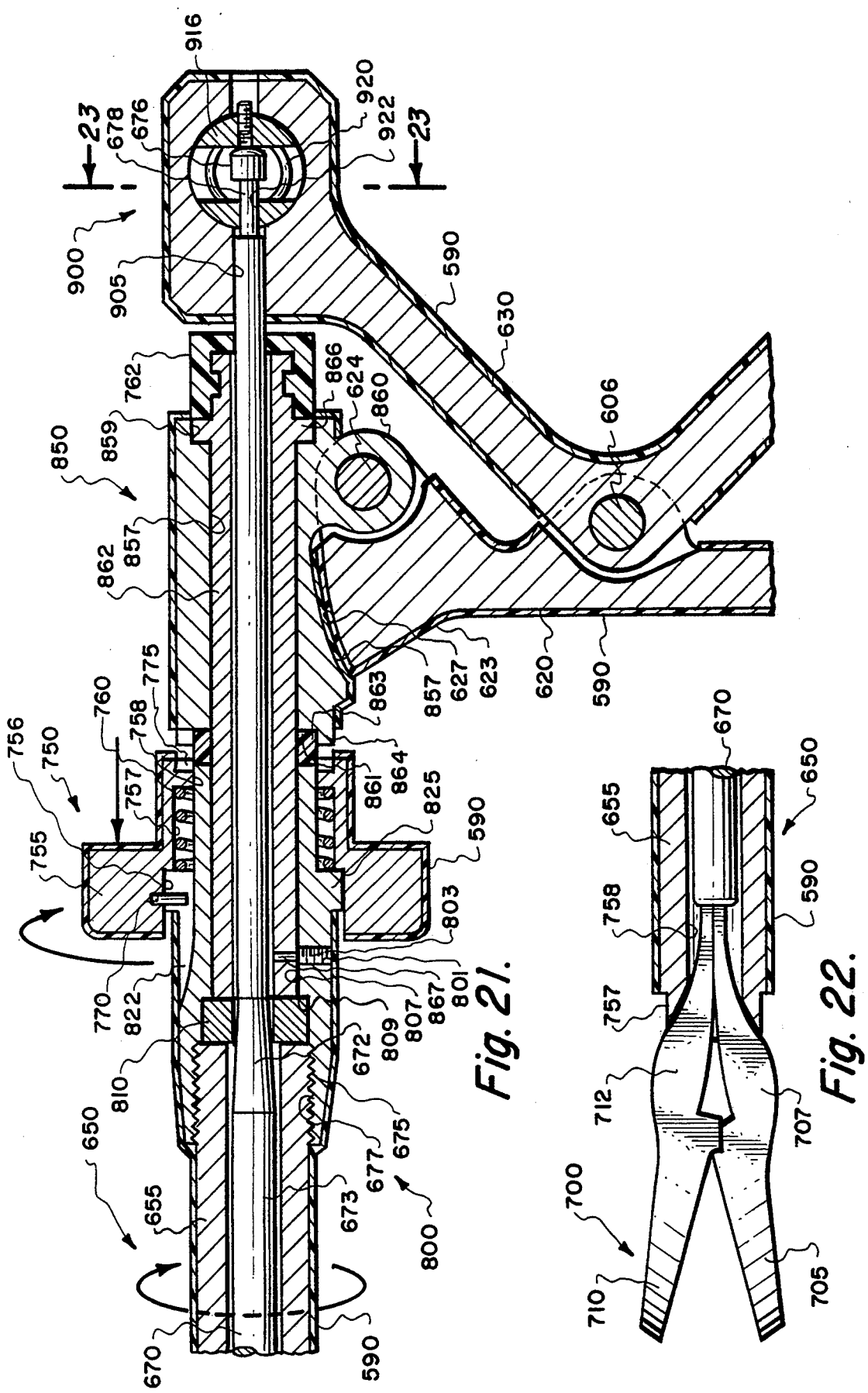

LAPAROSCOPIC GRASPER AND CUTTER

CROSS REFERENCE TO RELATED APPLICATION

This is a continuation-in-part of patent application Ser. No. 07/853,307, which was filed on Mar. 16, 1992, and is currently pending.

BACKGROUND OF THE INVENTION

1. Field of the Invention

The present invention pertains to the following areas of technology:

SURGERY—Medical and laboratory Equipment; hand-held or manipulated surgical instrument or tool for medical or laboratory use; surgical instrument used in laporoscopic surgery, for example, gall bladder surgery.

2. Description of the Prior Art

U.S. Pat. No. 4,174,715 issued to Hasson discloses a multi-pronged laparoscopy forceps.

U.S. Pat. No. 3,834,392 issued to Lampman et. al. discloses a complete laparoscopy system for female sterilization by tubal ligation.

Laparoscopic cholecystectomy is the term used to describe the removal of the gall bladder through a minimally invasive surgical technique. Several operations that once required an open incision of several inches can now be done by inserting a tiny video camera and microscopic instruments through small half-inch abdominal openings.

The gallbladder stores bile, which aids in the digestion of fats. Gallstones can form in the gallbladder causing inflammation of the gallbladder and blockage of the bile duct leading to the small intestine. Either condition can cause severe pain in the abdomen, accompanied by nausea and vomiting. Some experimental procedures deal with fracturing the gallstones with sound waves or dissolving the stones with chemicals. The most reliable treatment still available is surgical removal of the gallbladder. Patients can live without their gallbladders. The liver produces the bile, which continuously drips into the small intestine via the bile duct. The gallbladder stores concentrated bile as a backup in case the body needs extra bile after the patient eats a meal. The gallbladder connects to the bile duct. The absence of a gallbladder does not interfere with normal digestion. Conventional surgery requires a lateral 8-inch incision across the stomach, a six-day hospital stay, and at least a one-month recovery. The operation results in considerable postoperative pain and scarring. The new endoscopic procedure for gallbladder removal requires less invasive surgery, reducing the patient's discomfort, scarring, and reduced hospital stay.

The second most common laparoscopic procedure is hernia repair. A hernia is a weakness or tear in the abdominal wall. Some people are born with potential weakness, and when they lift a heavy object, tension forces the abdominal contents through the weakness or tear in the wall. Traditional hernia repair entails an incision in the groin, accompanied by two to six weeks recovery time. Laparoscopic techniques can now be done on an outpatient basis. A mesh is placed between the peritoneal lining and the muscles of the abdominal wall to reduce tension and eliminate the bulge. There is no open incision.

Splenectomy is the term used to remove the patient's spleen. The spleen is an organ designed to help fight infection in the body. But occasionally, the spleen can attack blood platelets. Hodgkin's disease may also require a splenectomy.

Laparoscopic techniques are also used for the following conditions: appendectomy; hiatal hernia repair; enterolysis for adhesions; and vagotomy.

SUMMARY AND OPERATION OF THE INVENTION

The present invention is a surgical instrument and is used in Laparoscopic Surgical techniques. Laparoscopy is a relatively new surgical procedure as described in the Background of the Invention. The surgical technique is used in the abdominal area. The term is derived from the Greek word for lap meaning flank. In the typical laparoscopic procedure, a trocar which is a tube with a pointed needle at one end, is inserted into the abdominal area through the navel. This point of entry is used to minimize any scaring. Small lateral incisions are also required to provide entry for other instruments including a miniature television camera or an optic light tube to allow the surgeon to view the inside of the abdominal cavity while the operation is in progress. This procedure is also used for diagnostic purposes and is used to enter the abdominal cavity to visually examine the internal organs. The abdominal cavity has to be expanded like a balloon to provide an area for the surgeon to work in. This is accomplished by the introduction of pressurized carbon dioxide gas through the trocar. The trocar has a valve on the exterior portion to attach to a pressurized carbon dioxide gas line of some type. The pressurized carbon dioxide gas enters through the trocar and into the abdominal cavity to expand the cavity. The hollow tube part of the trocar is used to allow the shaft of the laparoscopy instrument to be inserted. A seal at the exterior end of the trocar prevents the carbon dioxide gas from escaping.

The present invention is a laparoscopy instrument approximately 18 inches long and about 5 inches high. It has a cutting tip at its distal end, and a pair of handles at its proximal end. The shaft itself is about 0.25 inches in diameter. The sole purpose of this instrument is to provide a means for the surgeon to grasp or snip off a piece of organ or body tissue within the area being operated on. The end of the tubular shaft can either have a grasper or a cutter, which will close when the surgeon squeezes the pair of handles located at the proximal end of the instrument. The hollow shaft houses a movable solid shaft, which has the cutting or grasping tips at its distal end and an anchor point at its proximal end. The movable shaft can move slightly back and forth in the hollow shaft in a limited response to the surgeon squeezing the pair of handles. The movement opens and closes the tips as illustrated in FIGS. 18 and 20. One of the pair of handles has a barrel mounted on it. The other handle has a socket with a quick release button mounted on it. The socket receives and holds the ball end of the movable shaft to lock and maintain the end of the shaft in the socket. It also allows the shaft to be released quickly by simply depressing a release button to allow the movable shaft to be removed from the instrument. However, unless the button is depressed the socket grasps and maintains the end of the shaft and secures it while yet allowing the shaft to rotate. The hollow shaft is stationary relative to the movable solid shaft. When the handles are squeezed together, the distal end of the movable shaft is partially retracted into the rim of the hollow shaft to a depth of about 0.25 inches. This causes the pair of snipers or cutting blades to act like a pair of scissors closing together. Both blades have tapered outside edges adjacent to where each connects to the distal end of the inner shaft so that the pair of grippers or snipers are in effect squeezed together as the inner shaft is being pulled into the distal end of the outer hollow shaft. This retraction or pulling in is accomplished by the socket grasping the proximal end of the inner shaft in response to the handles being squeezes together. The outwardly tapered sides of the gripper or the snipper prevent either one from entering the hollow shaft to any appreciable extent. Sufficient clearance is provided at the distal rim of the hollow shaft to allow the grippers or snipers to be fully open when at the open at-rest position. When the shaft is pulled into the hollow shaft, the grippers or snipers close. This is the function of the instrument.

The pair of handles includes a locking means. As the surgeon is squeezing the handles together to close the grippers or the snipers, they will remain closed until the locking lever is depressed by the surgeon. The purpose of this is to keep a clamp on the grippers so that the surgeon can remove the discarded tissue or snipped off tissue and to remove it from the cavity of the patient.

Another novel feature of the present invention allows the surgeon to change the orientation of the grippers or snipers relative to the instrument. This is accomplished by a clutch means illustrated as a thumb wheel. The thumb wheel is secured to the upper end of the distal handle and at the proximal end of the shaft combination. By pulling proximally (first alternate) or distally (second alternate) on the thumb wheel, the clutch is disengaged. This procedure is illustrated in FIGS. 12 and 21. The surgeon then turns the thumb wheel to change the angular orientation of the cutting tips and releases the thumb wheel to reengage the clutch. A barrel combination, which includes a stationary barrel and a rotatable barrel, are also secured to the upper end of the distal handle. The barrel combination is located distally relative to the clutch means. The upper end of the distal handle contains a mounting means such as a yoke so that the stationary barrel can be secured to the yoke by a pair of opposed screws. The stationary barrel has attached to it a rotation means for rotating the cutting tip of the shaft. The stationary barrel remains stationary while the rest of the subassembly which comprises the shaft combination, the rotatable barrel, and the thumb wheel rotate the shaft and therefore the tip in about 5 degree increments either clockwise or counterclockwise. The upper portion of the proximal handle is angled or bent proximally relative to the distal handle. The two handles are pivotally secured to one another by a jeweler's screw. Each handle has a ring at its bottom for allowing the surgeon to grasp the handles like a pair of scissors. The upper end of the proximal handle also has a mounting means such as a yoke positioned in tandem with the yoke of the distal handle. The proximal yoke has the socket having a quick release button mounted on the yoke. The bore in the socket is in an axial alignment with the bore of the hollow shaft so that the ball end of the inner shaft can enter and pass through the bore of the socket. The quick release button on the socket secures and locks the ball and of the inner shaft but it still permits the angular orientation of the grippers or cutting blades to be changed by rotating the thumb wheel.

Another novel feature of the present invention allows the movable inner shaft containing the grippers or scissors to be quickly removed and replaced with another shaft to increase the versatility of the present invention. This is illustrated in FIG. 13. The present invention can be quickly disassembled, cleaned, sterilized, and reassembled for the next operation. It can also be easily repaired or refurbished at minimal cost. By simply depressing the quick release button in the socket mounted at the upper end of the proximal handle, the solid shaft can be removed from the rest of the instrument by pulling on the gripper or cutter ends and pulling out the inner shaft from the outer hollow shaft. FIGS. 13, 23 and 24 illustrate the quick release button being depressed. A replacement shaft having the same dimensions can then be quickly inserted in the hollow shaft and pushed into the socket and secured therein. The instrument is ready to be used again with another shaft and attached grippers or cutting blades.

Yet another novel feature of the present invention is the angular orientation of the two handles and the respective mounting yokes. This unique angular orientation results in the hollow barrel remaining stationary while the grippers or snipers are being pulled into the shaft during the cutting or grasping stages of the operation. The surgeon is better able to control the cutting, gripping, grasping or pulling activity because only the tips move. When the handles are squeezed together by the surgeon during the operation, the socket is pulled proximally relative to the stationary hollow shaft. The hollow shaft and supports remain stationary while the cutting blades are cutting tissue.

In the second alternate of the present invention illustrated in the drawings, the laparoscopy instrument has been modified to allow electrical current to be passed through to the cutting tips. The second alternate can be described as a monopolar electrocautery laparoscope. The second alternate can be used in a cauterization procedure such as in tubal ligation. An electrical current flows to the tips allowing electrical current to burn or cauterize the target tissue in the abdominal cavity, as selected by the surgeon. The instrument must be electrically insulated to protect everyone including the surgeon from shock. This is accomplished by having the outer portions including the pair of handles, the thumb wheel, the outer shaft, and the barrel means all coated with an electrically insulating vinyl material. A means for plugging in an electrical cord, and an electrical conduction to the metallic cutting blades are necessary. In the second alternate, the quick release button securement means has become integral with the top of the proximal handle. The distal handle is pivotally connected to the bottom of the barrel rather than having a yoke as disclosed in the first alternate.

Accordingly, it is an object of the second alternate or variant of the present invention to provide an electrically insulated laparoscopy instrument which can be used to cauterize a patient without creating electrical shock to the patient or the surgeon while using the instrument during the operation. The tips act as the ground for the flow of electricity. The current flows from the tip of the instrument to the area adjacent the placement of the tip. Heat is generated by the electricity at this point causing cauterization.

BRIEF DESCRIPTION OF THE DRAWINGS

FIG. 1 is a left side elevational view of the first alternate of the present invention.

FIG. 2 is a fragmentary right elevational view of the handle portion of the first alternate of the present invention.

FIG. 3 is a top plan view of FIG. 1.

FIG. 4 is bottom plan view of FIG. 1.

FIG. 5 is a longitudinal sectional view taken along line 5——5 in FIG. 3.

FIG. 6 is a transverse sectional view taken along line 6——6 in FIG. 5.

FIG. 7 is a sectional view taken along the line 7——7 in FIG. 5.

FIG. 8 is a sectional view taken along line 8——8 in FIG. 5.

FIG. 9 is a sectional view taken along line 9——9 in FIG. 5.

FIG. 13 is similar to FIG. 5 and illustrates the shaft being separated from the socket to remove the shaft with the attached cutting blades.

FIG. 14 is a left side elevational view of the second alternate of the present invention.

FIG. 15 is top fragmentary view of the handle portion of the second alternate of the present invention taken along line 15—15 in FIG. 14.

FIG. 16 is a top fragmentary view of the cutting tip portion of the second alternate of the present invention taken along line 16—16 in FIG. 14.

FIG. 17 is a longitudinal sectional view taken along line 17—17 in FIG. 15 illustrating the handles in an at-rest open position.

FIG. 18 is a longitudinal sectional view taken along line 18—18 in FIG. 16.

FIG. 19 is similar to FIG. 17 and illustrates the handles being squeezed together to retract the solid shaft to close the cutting blades.

FIG. 20 illustrates the cutting blades being closed by the action shown in FIG. 19 in response to the handles being squeezed together.

FIG. 21 illustrates the shaft, barrel, and clutch means of the second alternate instrument being rotated 180 degrees relative to the position shown in FIG. 17 to change the angular orientation of the cutting blades also by 180 degrees.

FIG. 22 illustrates the new orientation of the cutting blades after the rotation shown in FIG. 21.

FIG. 23 is a transverse sectional view taken along the line 23—23 in FIG. 21 and illustrates the quick release button in the socket engaging the end of the cutting blade shaft to lock the shaft in the socket.

FIG. 24 is a view similar to FIG. 23 illustrating the quick-release button being depressed in order to release the end of the shaft having the cutting blades and then to remove the shaft from the instrument.

DETAILED DESCRIPTION OF THE PREFERRED EMBODIMENT

Figure 11:
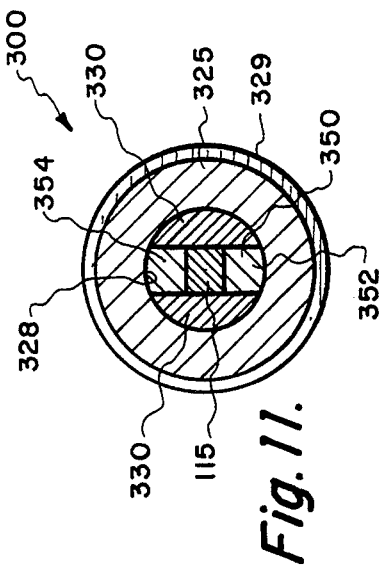
FIG. 11 is a sectional view taken along line 11——11 in FIG. 5.

The present invention will now be discussed in greater detail. FIGS. 1-4 illustrate the first alternate or a variant of the present invention. FIG. 1 is the left side elevational view illustrating the cutting tips at the distal end and the pair of handles at the proximal end. The instrument is about 16 inches long and about 4 inches high. The major components comprising the first alternate of the present invention are: a pair of squeeze handles 10 and 20; a shaft combination 100; cutting tip means 50; a clutch means 200 to rotate the shaft combination; barrel means combination means 300 for supporting the rotatable shaft and clutch; and socket means 400 with a quick release button 410.

Figure 12:
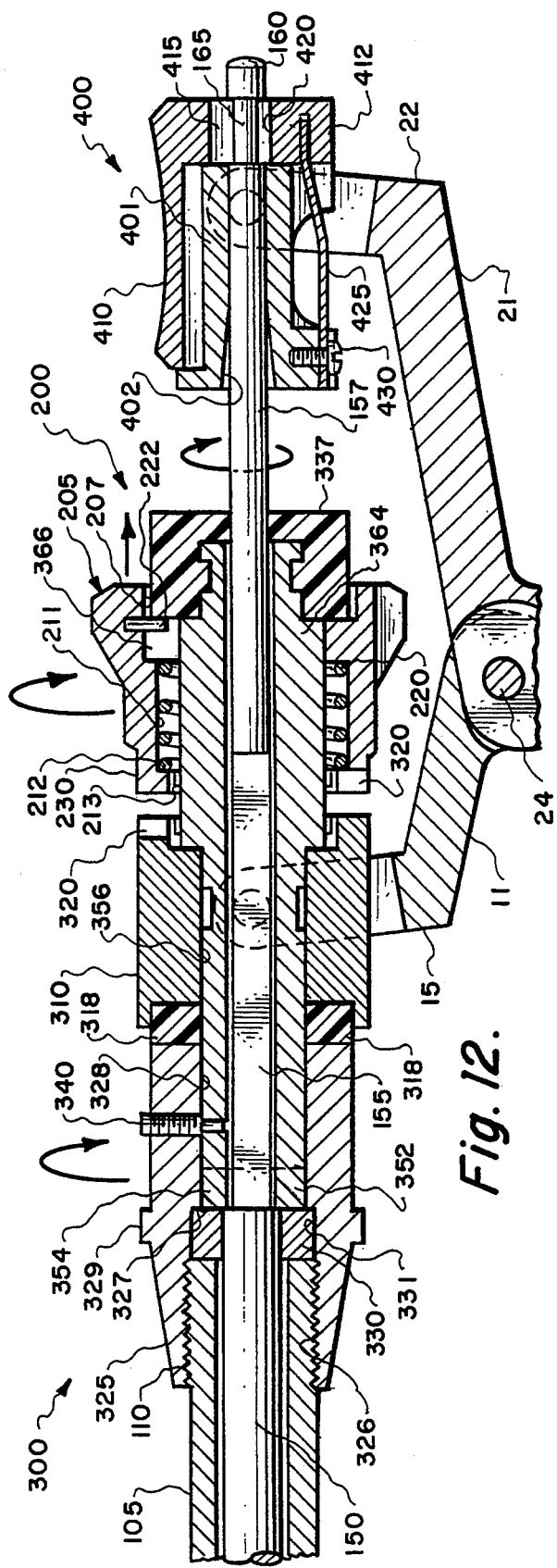
FIG. 12 illustrates the body of the instrument being rotated 180 degrees relative to the position shown in FIG. 5 to change the angular orientation of the cutting blades.

FIGS. 5, 12, and 13 illustrate the rotatable shaft combination 100, which includes an outer hollow tubular shaft 105, and an inner solid cylindrical shaft 150. The tubular shaft 105 has a proximal male threaded end 110 for threaded insertion in the distal end of the barrel combination means 300. The distal end of the barrel combination has a threaded female cylindrical opening 326 for receiving the male end 110 of the shaft 105. The shaft 105 is hollow throughout and has both ends open to house the inner solid shaft 150 and to allow the inner shaft 150 to reciprocate therein. The distal end of the inner solid shaft 150 has cutting or gripping means illustrated as a pair of opposed curved scissor-like blades labelled 55 and 75. The pair of blades forms a Y-shaped configuration with the end of the shaft 150. Each blade is secured to the end of the shaft 150 with a flexible arm 57 and 77 respectively and are angled outwardly from the axis of the shaft 150. Both arms 57 and 77 taper as they merge at the distal end of the shaft 150. As the distal end of the shaft 150 is pulled into the hollow shaft 105 by the squeezing of the pair of handles 10 and 20, the tapered arms 57 and 77 flex together like a tweezers at the distal opening of the hollow shaft 105 causing the pair of cutting blades 55 and 77 to close to cut any tissue placed between the open blades.

The inner solid movable shaft 150 has a distal larger cylindrical portion 151 until a flat square portion 155 is formed towards the shaft's proximal end. The square portion 155 is formed by flattening the surface of the shaft 150 to form four flat mutually opposed faces. A cylindrical portion 157 having a diameter less than the other cylindrical portion 151 of the shaft extends from the proximal end of the flat portion 155 to the proximal end of the shaft 150. The diameter of the cylindrical portion 157 is the same as the thickness between either opposed face on the square portion 155. The movable shaft 150 has a securement means at its proximal end. The securement means is illustrated as a ball-like tip 160. It is formed by a annular groove 165 cut in the cylindrical portion 157 inboard from the proximal end of the movable shaft 150. These features are clearly illustrated in FIG. 13. The securement means is used to engage and lock the proximal end of the movable shaft 150 to the socket 400.

The socket, collectively labelled 400, is clearly illustrated in FIGS. 5-7. The socket 400 is mounted on the yoke 22 or brace of the proximal handle 20. A pair of opposed jeweler's screws 405 and 407 extend through both sides of the yoke 22 and are screwed into the sides of block 401 of the socket 400 to form a swivel joint between the socket 400 and the yoke 22 to allow the socket to swivel up and down when necessary. The socket 400 has an axial bore 402 passing therethrough, which is axially alignable with the movable shaft 150. The socket 400 includes an L-shaped spring loaded quick release button and lock combination 410. The rear vertical track portion 412 of button 410 is movable vertically in a channel 414 cut into the proximal end of the socket 400. The button 410 has a vertical rear or proximal keyhole-shaped opening 415 in the vertical portion 412 of the button 410. The keyhole opening is aligned with the bore 402 so that the ball end 160 of the movable shaft 150 can pass through the bore 402 in the socket and through the larger circular portion 418 of the keyhole opening 415 in vertical portion 412 of the button 410. The smaller slotted portion 420 of the keyhole 415 is the same width as the annular groove 165 adjacent the ball end 160 on the shaft 150. The slotted portion 420 of the keyhole 415 mates with the annular groove 165 on the shaft to lock and hold in position the ball end 160 of the shaft 150 in the quick release button 410 of the socket 400. The vertical portion 412 of the button 410 is biased upwardly by a flat spring 425, which is secured to the underside of the socket 400 with a jeweler's screw 430. The spring 425 maintains upward force against the vertical portion 412 of the quick-release button 410. The upward force presses the slotted portion 420 of the keyhole opening 415 against the annular groove 165 of the shaft causing the shaft 150, which is in the bore 402 of the socket, to be forced against the upper wall of the bore 402 in the socket 400. The bore 402 maintains the shaft 150 in position. It also maintains the grooved portion 165 of the shaft in the slotted keyhole portion 420 of the button 410. This locks the ball end 160 of the shaft 150 in place. By depressing the button 410, the ball end 160 of the shaft 150 can be removed from the socket 400. FIG. 13 illustrates the depressing of the quick release button 410 by means of a vertical arrow pointed at the button 410 during the removal of the ball end 160 of the shaft 150 from the socket 400. However, unless the button 410 is depressed, this locking means still allows the shaft and ball end 160 of the shaft 150 to rotate even while the ball 160 is locked in place as illustrated in FIGS. 5—7. As the socket 400 travels distally and proximally in response to the handles 10 and 20 being squeezed, the movable shaft 150 reciprocates proximally or distally the same amount. The whole purpose of this reciprocal distal-proximal lengthwise movement of the movable shaft 150 is to cause the cutting tip means or gripper means 50 to open and close at the distal end of the shaft 150.

Figure 10:
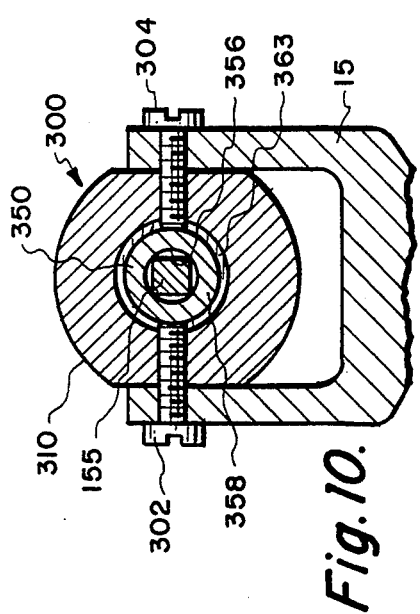
FIG. 10 is a sectional view taken along line 10——10 in FIG. 5.

The clutch means, collectively labelled 200, and the barrel means, collectively labelled 300, will now be discussed in greater detail. The barrel means is mounted to the mounting means illustrated as a yoke or brace 15 at the upper end of the distal handle 10. A pair of opposed jeweler's screws 302 and 304 extend through both sides of the yoke 15 and are screwed into the flattened sides of the barrel means 300 to secure the barrel means in the yoke, and to form a swivel joint between the barrel means 300 and the yoke 15 to allow the barrel means to swivel up and down whenever necessary. This is clearly illustrated in FIG. 10.

The barrel means 300 and clutch means 200 combination comprise the following components: a cylindrical-shaped stationary barrel 310 mounted on the yoke 15 of the distal handle 10; a movable barrel 325 positioned distally of the stationary barrel 310; a cylindrical-shaped internal cartridge 350; thumb wheel 205; locking ring 310; coil spring 335; and a Torlon ring 337.

The stationary barrel is labelled 310. Since this part is secured to the yoke 15 of the distal handle 10, this part cannot rotate about its axis. The stationary barrel 310 is cylindrical-shaped and has an axial bore 312 running therethrough. Both open ends of the stationary barrel have enlarged bore openings. The distal larger bore opening is labelled 316 and the proximal larger bore opening is labelled 314. A bushing or rubber sealing ring 318 is positioned in the larger distal bore opening. The bushing 318 has an axial bore of the same diameter as does the axial stationary bore 312. Radially cut teeth 320 are located on the proximal face and circumvent the proximal larger bore 314 of the stationary barrel 310.

The distal movable barrel labelled 325 is aligned with the stationary barrel 310 and positioned distally from the stationary barrel. An axial bore having a larger threaded distal bore 326 and a smaller smooth proximal bore 328 passes through the movable barrel 310. An annular rib 329 is located on the outside surface midway between both ends. The distal bore 326 is threaded for threadably connecting with the threaded end 110 of the hollow shaft 105. The inner terminus of the threaded portion 326 of the movable barrel then becomes a smooth bore 331 until it reaches an annular shelf 327 or ledge resulting from the proximal bore portion 328 being reduced in diameter relative to the larger threaded portion 326 and smooth portion 331 of the bore of the movable barrel. The proximal portion 328 of the stationary bore is smooth and is slightly smaller than the overall outside diameter of the hollow shaft 105. An annular locking ring 330 having a diametral transverse slot 332 is located in the smooth distal portion 331 of the bore and abuts against the annular shelf 327 inside the movable barrel. The locking ring 330 has the same overall dimensions as does the smooth distal portion 331 so that it securely fits in place there. The proximal end of the threaded end 110 of the hollow shaft abuts against the distal face of the locking ring 330 to keep the ring 330 in position, and yet to allow the ring to freely rotate when necessary. The diametral transverse slot 332 of the locking ring 330 faces proximally towards the stationary barrel 310. The ring 330 has a bore of sufficient diameter to slip over and slide along the square portion 155 of the movable shaft 150. However, the diameter is smaller than the diameter of the cylindrical portion 157 distal from the square portion 155 of the inner shaft 150. The locking ring 330 stops at the end of the square portion 155, because it cannot slide onto the distal cylindrical portion 157 of the movable shaft 150. The ring 330 cannot travel beyond the proximal end of the square portion 155 of the movable shaft 150. Additionally, the diameter of the bore of the ring 330 is sufficiently small to prevent the ring 330 from rotating about the square portion 155. It can slide back and forth along the square portion, but it cannot rotate about the square portion.

The cylindrical-shaped cartridge 350 will now be discussed in greater detail. The internal cartridge 350 is about 1.5 inches in length. It is positioned in the barrel combination formed by both the stationary barrel 310 and the movable barrel 325. The distal end or tip 352 of the cartridge 350 has a pair of opposed secant flats 352 and 354 removed from the cylinder wall at the distal tip. The distal cut tip of the cartridge 350 mates with the slot 332 in the proximal face of the locking ring 330. The cartridge 350 and the locking ring 330 can slide lengthwise within a limited range relative to each other, but both must rotate in unison. The mated ends of the cartridge 350 and the locking ring 330 function as a type of slip joint. The slip joint is necessary to provide a limited amount of lengthwise clearance when the clutch means 200 is temporarily disengaged to rotate the inner shaft 150 to allow the angular orientation of the cutting blades 50 to be changed by the surgeon.

The cartridge 350 has an axial bore 356 running therethrough. Reference numerals for the cartridge 350 are placed in FIG. 13. FIG. 13 illustrates the inner shaft 150 being unlocked and withdrawn from the socket 400 while also being withdrawn from the hollow shaft 105. This procedure is used to remove the cutting tips and replace them with a new pair of cutting tips, or to remove the tips to clean them and then to reinsert them. The diameter of the bore 356 in the cartridge is sufficient to allow the square portion 155, the proximal cylindrical portion 157 and the ball end 160 of the inner shaft 150 to pass through. However, the secant flat faces at the tip or distal end 352 of the cartridge 350 prevents the larger cylindrical portion of the inner shaft 150 from passing through. The outside cylindrical wall of the cartridge 350 contains a first cylinder surface 358 that mates with the bore 305 in the movable barrel 310. The larger stepped outside cylinder surface 360 positioned proximally from the smaller outside surface 358 mates with the bore 207 of the thumb wheel 205. The two cylinder sections 358 and 360 transcend to form an annular ridge 362 at the edges where the two cylinder surfaces 358 and 360 meet. This ridge abuts against the rim formed at the opening of the larger bore 314 at the proximal end of the bore of the stationary barrel 310. This prevents the remainder of the cartridge 350 from penetrating any further into the bore of the stationary barrel 310 beyond that point. The ridge 362 and the rim at the larger bore 314 act as a stop. The outside surface 358 of the small cylindrical portion of the cartridge 350 also has a shallow flat annular groove 363 cut into its surface.

The proximal end of the cartridge 350 has a large annular flange 364. The flange 364 also has an axial notch 366 cut into the outside rim of the flange 364. This flange 364 cooperates with the interior bore 207 of the thumb wheel 205. The proximal end of the cartridge has a nipple 368. A small shallow exterior annular groove is cut inboard from the nipple. The nipple 368 has a Torlon cylindrical ring 337 secured to it. The flexible and stretchable Torlon ring 337 has an axial bore 339 running therethrough. The inner shaft 150 passes through the axial bore 356 of the cartridge 350, and then through the bore 339 of the Torlon ring 337. The Torlon ring 337 functions as a pneumatic seal to minimize the leakage of carbon dioxide air from the inner shaft 150 when the instrument is in use. The Torlon ring 337 also functions as a bushing. The distal end of the cartridge 350 has a small transverse radial hole 370 drilled in the smaller cylindrical wall 358. The movable barrel 325 also has a complementary transverse radial hole 327. After the barrel 300 and clutch means 200 are assembled on the instrument, a small set screw 340 or rivet is placed in both holes 370 and 327. This keeps the assembly locked together.

The thumb wheel 205 has the general overall appearance of a frusto-conical section. The proximal portion of the thumb wheel is star-shaped having a plurality of radially spaced apart rounded projections 207 with semicircular indentations 209 formed between the projections 205. The thumb wheel surface is designed for easy gripping by the surgeon while he or she is wearing latex gloves and using the present invention during an operation. The projections 207 form an array of nubs.

The thumb wheel 205 has three stepped bores forming the overall bore. The bores are labelled 209, 211, and 213. All three bores are in a spaced apart axial alignment with each other. The smallest bore 213 is located distally in the overall bore. The smallest bore 213 is the same diameter as the bore in the stationary barrel 310. The second larger bore 211 is the same diameter as a coil spring 220 placed in the thumb wheel 205. The transition point where the smaller bore 213 meets the medium bore 211 forms an annular seat 212 where the distal end of the coil spring 220 can abut against. The large bore 209 mates with the large flange 364 on the cartridge 350. The surface of the large bore has a radial projection 222 that mates with the longitudinal cut 366 on the flange on the cartridge 350. These two parts 222 and 366 function like key and keyway to force the cartridge 350 and thumb wheel 205 to rotate in unison, and also act as a guideway to allow the cartridge 350 to slide back and forth within a limited range in the thumb wheel 205. The inside face of the cartridge 350 acts as a seat for the proximal end of the coil spring 220. The coil spring 220 fits over the large cylinder portion 360 of the cartridge. The coil spring 220 has a diameter slightly smaller than the diameter of the medium bore 211 in the thumb wheel 205. The coil spring 220 occupies the space between the medium bore 211 in the thumb wheel 205 and the larger cylinder 360 on the cartridge 350. After the components forming the barrel means 300 and clutch means 200 are assembled, the coil spring 220 is compressed and is under constant tension. It caused the thumb wheel 205 to be continuously biased against the proximal face of the stationary barrel 310.

As previously stated, the proximal face of the stationary barrel 310 has a circumferential array of radial teeth 320 cut into its face. The distal end of the thumb wheel 205 also has a face with a circumferential array of radial teeth 230 cut into its face. Both sets of teeth are complementary and mesh together like a set of gears. The biasing of the coil spring 220 forces both sets of teeth 320 and 230 to continuously mesh together to effectively lock the thumb wheel 205 to the stationary barrel 310. This in turn prevents the inner shaft 150 from rotating. The cutting tips 50 extending from the distal end of the inner shaft 150 cannot change their angular orientation unless the inner shaft 150 is rotated. The thumb wheel 205 and the associated parts function like a clutch means 200 to allow the inner shaft 150 to rotate to allow the surgeon to change the angular orientation of the cutting tips 50. By simply turning the thumb wheel 205 a few degrees at a time, the angular orientation of the cutting tips 50 is changed the same number of degrees. The spacing of the teeth determines the minimum angular change. However, the spacing between adjacent teeth of the teeth arrays 320 and 230 is sufficiently small so that the increments are very small. If the surgeon rotates the thumb wheel 205 a quarter of a turn the angular orientation of the tips 50 is changed ninety degrees. If the surgeon rotates the thumb wheel 205 one-half of a turn, the angular orientation of the cutting tips 50 is changed 180 degrees. Since the thumb wheel 205 can rotate clockwise or counterclockwise, the surgeon need only turn the thumb wheel a half a turn at most to set the angle of the tips to any desired angle. While turning the thumb wheel the facing teeth 230 on the thumb wheel 205 move away from the teeth 320 on the stationary barrel 310 until adjacent teeth depressions are reached. The teeth are formed by very small V-shaped cuts in the faces. The facing teeth ride up on each other to the crest of each tooth then fall back together after passing the crest. The spaces between the teeth can be referred to as lands. The teeth mesh by having the crest on one face mating with the depression or land on the other face. The movement between the lands and the crests causes a clicking sound. This audible clicking sound helps the surgeon to judge how far to turn the thumb wheel 205. After using the instrument for some time, the surgeon can judge the angular change by associating it with the number of clicks. The coil spring forces the thumb wheel 205 against the stationary barrel 310 to make a clicking noise as the thumb wheel is rotated.

The pair of handles will now be discussed in greater detail. The pair of handles are labelled 10 and 20. The distal handle 10 has a finger ring at its bottom and a yoke at its top. As previously discussed, the yoke 15 holds the stationary barrel 310 in place. About two thirds up from the base, the handle 10 makes a forward bent angle of about forty degrees from the rest of shank of the handle 10 to form a bent portion 11. The area of the bending is enlarged to strengthen the rigidity of the handle and to form an area where the two handles can be pivotally secured with a set screw 24. The proximal handle forms a mirror image with the distal handle 10 up to the area where the two are pivotally connected to one another. All the drawings illustrate both handles in an open position. If one were to squeeze both handles together so that they touch each other, the mirror image relationship could be readily observed. The proximal handle 20 also has a bent portion 21 above the pivot point. The bent portion is bent downwardly forming about a seventy five degree between the lower portion and the bent portion. As previous discussed, the bent portion has a yoke 22 for mounting the socket 400.

After the instrument is assembled as shown in FIG. 1, the pair of handles are not in vertical relationship to the shaft combination 100, but are angled away from the shaft combination. This angled combination is very important to the present invention. When the surgeon squeezes the pair of handles to cut a piece of tissue, the position of the end or tip 50 of the instrument remains stationary for the surgeon. The bases 57 and 77 of the cutting tips 55 and 75 retract into the hollow tube 105 forcing the cutting blades 50 to close like a pair of scissors to cut the tissue. The blades move, but not the stationary tip. Because the laparoscopic procedure is being done inside the patient, the surgeon cannot actually see what he is cutting with the instrument. He move rely on the images formed on the television monitor that are relayed from a tube or miniature camera in the patient. Because the instrument does not move during the cutting process, the field of view on the screen keeps the tips in view so that the image transmitter does not have to be realigned for the image receiver.

The handles 10 and 20 have a locking means to lock the handles together after the surgeon has squeezed the handles together to close the grippers or the pair of scissors at the tip of the shaft 150. The locking means is illustrated as a ratchet and pawl. The ratchet 27 is bow-shaped with a series of ratchet teeth 29 on the upper edge of the bow. The pawl is positioned in a vertical slot 30 in the proximal handle 20. A release lever 30 is mounted on the distal handle 10. By depressing the lever 30, the ratchet 27 also bends down releasing it from the pawl 34 in the slot. The slot 30 is large enough and surrounds the bow-shaped ratchet to allow reciprocal movement of the handle 20 relative to the ratchet. The surgeon simply depresses the lever 30 while pulling on the handle 20 to open the handles while at the same time opening the gripers or snipers. Releasing the lever then cocks the instrument in the open position. The handles can be squeezed in steps as the pawl goes from one ratchet tooth 29 to the next. The tension at the cutting tips 50 at the distal end of the inner shaft tends to counteract any squeezing force on the handles so that the handles will not close by themselves spontaneously.

The second alternate of the present invention is illustrated in FIGS. 14–24. The second alternate has the following modifications relative to the first alternate previously discussed. The handles 600 and 620, outer shaft 650, socket 900, barrel combination 800, and clutch means 750 are all covered with an electrical insulating type of material 590. The proximal handle 600 has an electrical receiving plug means 602 so that the tip of an insulated electrical conducting cord 604 can be plugged into the instrument.

Laparoscopic procedures commonly include cauterization where the tissue is seared or burned with a hot tip. Tubal ligation involves cauterization of the fallopian tubes or oviducts to sterilize a female patient. The exposed metal cutting tips 700 extending from the distal end of the hollow shaft 655 act as an electrical conducting tip when an electric cord is plugged into the instrument to pass electricity to the tips. The electric current travels to the tissue adjacent the metal tips 700 causing an electric arc and resultant heat. The insulation 590 coating on the instrument prevents electric shock to the surgeon or the patient. When the electric cord 604 is not plugged into the instrument or if the cord is switched off, the instrument can be used in the same manner as the first alternate of the present invention.

The socket 900 has been modified so that there is a side release button 914 to release the ball end 676 of the inner shaft 670 from the hollow shaft 655. The inner shaft 670 having the cutting the tips 700 at its distal end does not have a square portion along any portion of its length. Instead, a tapered portion 672 is present between the larger cylindrical distal portion 673 and the smaller cylindrical proximal portion 674. The locking ring has been modified. It is now a pair of notches at the distal end of the hollow shaft 655. The distal tip of hollow shaft extends about a quarter of an inch beyond insulating material 590 as illustrated in FIGS. 18, 20, and 22. The exposed end 755 of the hollow shaft has a diametral transverse slot 758 cut about one-eighth inch into the tip. This slot 758 mates with the tapered edges of the cutting tips 707 and 712. This arrangement allows for a smoother closing of the cutting blades when the surgeon squeezes the handles. The thumb wheel 750 has been changed so that the thumb wheel 750 slides distally to disengage the barrel means 800 in order to rotate the thumb wheel 755 and the shafts 650 and 655 to change the angular orientation of the cutting tips 700.

The alternate of the present invention will now be discussed in greater detail. FIGS. 14–22 illustrate the second alternate or variant of the present invention. The second alternate can be described as a monopolar electrocautery instrument. FIG. 14 is the left side elevational view. The instrument is about 16 inches long and about 4 inches high. The major components comprising the second alternate of the present invention are: a pair of squeeze handles 600 and 620; a rotatable shaft combination 650; cutting tip means 700; a clutch means 750 to rotate the shaft; movable barrel means 800, and the stationary barrel means 850 for supporting the rotatable shaft and clutch; and a socket 900, with a quick release button 914, for causing reciprocal movement of the shaft having the cutting blades.

The rotatable shaft combination, collectively labelled 650, includes an outer hollow tubular shaft 655, and an inner solid cylindrical shaft 670. The tubular shaft 655 has a proximal male threaded end 675 for threaded insertion in the distal end of the movable barrel combination 800. The distal end of the movable barrel combination 800 has a threaded female cylindrical opening 855 for receiving the male end 675 of the shaft 655. The shaft 655 is hollow throughout and has both ends open to house the solid shaft 670 and to allow the inner shaft 670 to reciprocate therein. The distal end of the inner solid shaft 670 has cutting or gripping means collectively labeled 700. The gripping or cutting means are illustrated as a pair of opposed curved scissor-like blades labelled 705 and 710. The pair of blades forms a Y-shaped configuration with the end of the shaft 670. Each blade is secured to the end of the shaft 670 with a flexible arm 707 and 712 respectively and are angled outwardly from the axis of the shaft 670. Both arms 707 and 712 taper as they attach at the end of the shaft. Both arms are locked in the diametral slotted opening 758 of the exposed end 757 of the hollow shaft 655. As the distal end of the shaft 670 is pulled into the hollow shaft 655 by the squeezing of the pair of handles 600 and 620, the tapered arms flex together like a tweezers at the distal opening of the hollow shaft 655 causing the pair of cutting blades to close to cut any tissue placed between the open blades. The slotted tip 758 acts as a guideway for the tapered arms. The movable shaft 670 is cylindrical in shape until a tapered portion 672 is formed towards the shaft's proximal end. A cylinder portion 674 having a diameter less than the other cylinder portion of the shaft extends from the proximal end of the tapered portion 672 to the proximal end of the shaft 670. The diameter of the cylinder portion 674 is less than the distal end of the shaft 670. The movable shaft 670 has a securement means at its proximal end. The securement means is illustrated as a ball-like tip 676. It is formed by a annular groove 678 cut in the cylindrical portion 674 inboard from the proximal end of the movable shaft 670. The securement means is used to engage and lock the proximal end of the movable shaft 670 to the socket 900.

The socket 900 is clearly illustrated in FIGS. 21, 23–24. The socket 900 is integrally mounted at end of the brace 630 of the proximal handle 600 and has the appearance of a pod projecting from the upper end of the proximal handle 600. The socket 900 has a horizontal longitudinal bore 905 therethrough, which is axially aligned with the movable shaft 670. The socket includes a transverse cylindrical cavity 910 shown in cross section in FIGS. 23–24. A cylinder-shaped quick release button 914 having the same diameter as the cavity but being slightly longer than the depth of the cavity 910 is slidably mounted in the cavity. The head of the button 914 protrudes out of the cavity as illustrated in FIG. 23. The other end or base of the button has a deeply cut diametral slot terminating at the head. The distal inside face of the slot is illustrated in FIGS. 23–24. The base of the button 914 has a circular depression 918 for receiving one end of a coil spring 920. The other end of the spring 920 mounts flush against the bottom of the cavity 910. This makes the button 914 spring loaded. The compressed coil spring 920 pushes against the base of the button in an attempt to eject the button from the cavity. However, the button is held in place in the cavity because of the ball end 676 of the shaft 670 being positioned in the diametral slot 916. The slot divides the shank portion of the button in two opposed halves. The distal half has a transverse keyhole-shaped opening 922 cut through the half. The larger circular portion of the opening 922 allows the ball end 676 of the movable shaft 670 to pass through and to reside in the diametral slot 916. This is clearly illustrated in FIG. 17. The smaller slotted portion of the opening allows the annular groove 678 of the shaft to slide back and forth in. This arrangement locks the ball end 676 of the shaft in place unless the button 914 is depressed. The cylindrical portion 674 of the movable shaft 670 is the same diameter as the bore 905 in the socket. This prevents the shaft 670 from moving laterally in the bore 905. The slotted portion of the keyhole opening 922 maintains a constant lateral force against the shaft 670 while at the same time preventing the ball end 676 from slipping out. The compressed coil spring 920 is the source of the transverse force. By depressing the head of the button 914, the keyhole opening 922 moves transversely allowing the ball end 676 to pass through the larger circular portion in the keyhole opening 922. The shaft 670 can be pulled out of the instrument by pulling on the cutting tips 700. The shaft and the rest of the instrument can be cleaned and sterilized and assembled for reuse. A replacement shaft can also be quickly inserted in the instrument. The ball end 676 of the replacement shaft is first inserted in the rim of the hollow shaft 655 and then pushed until the ball end 676 emerges from the barrel 850. The ball end is then guided into the bore 905 of the slot while the quick release button 914 is depressed. One can feel the ball end 676 click into place. The button 914 is then released to lock the ball end of the shaft 670 in the socket 900. The keyhole opening is aligned with the bore 905. FIG. 24 illustrates the depressing of the head of the quick release button 914 during the removal of the ball end 676 of the shaft 670 from the socket 900. However, the locking connection still allows the shaft and ball end and shaft 670 to rotate even while the ball is locked in place as illustrated in FIG. 23. As the socket reciprocates lengthwise in response to the handles 600 and 620 being squeezed, the movable shaft 670 reciprocates lengthwise the same amount. The whole purpose of this reciprocal lengthwise movement of the removable shaft is to cause the cutting tips or grippers 700 to open and close at the distal end of the shaft 670.

The clutch means 750, movable barrel means 800, stationary means 850 and will now be discussed in greater detail. The stationary barrel means 850 is illustrated as a generally rectangular piece of metal 855 having a bore therethrough. It is pivotally mounted to the brace 623 of the front handle 620. The top of the brace has an arcuate-shaped surface 627 with a transverse mounting hole located proximally on the brace. The underside of the barrel 855 has a longitudinal arcuate-shaped depression 857 and a proximal projection 860. The curved surface 627 of the brace 623 is complementary with the arcuate surface depression 857. The mounting hole on the brace 623 and the hole in the projection 860 are pivotally connected by a pivot pin 624. The front handle 620 can freely pivot proximally, or rearwardly. However, the arcuate surface 627 and the arcuate depression 857 restrict and stop the front handle from pivoting distally beyond a certain point. The distal handle stops its distal swinging motion when the handle is about at a right angle relative to the shaft means 650. The swivel joint between the stationary barrel 855 and the handle 620 allows the barrel 855 to pivot up and down and the handle 620 to pivot back and forth whenever necessary.

The stationary barrel means, the movable barrel means and clutch means combination comprise the following components: a rectangular-shaped stationary barrel 855 mounted on the brace of the distal handle 620; a rotatable barrel 805 positioned distally of the stationary barrel 855; a cylinder-shaped cartridge 862; thumb wheel 755; sealing ring 863; coil spring 760; a stop ring 10; and a Orlon ring 762.

The stationary barrel is labelled 855. Since it is secured to the brace 623 of the distal handle 620, this part cannot rotate about its axis. The stationary barrel 855 is rectangular-shaped and has an axial bore 857 running therethrough- Both open ends of the stationary barrel have enlarged bore openings. The proximal larger bore opening is labelled 859 and the distal larger bore opening is labelled 861. A bushing or rubber sealing ring 863 is positioned in the larger distal bore opening 861. The bushing has an axial bore of the same diameter as does the axial stationary barrel bore 857. Radially cut teeth 864 are located on the distal face and circumvent to the distal larger bore 861 of the stationary barrel 855.

The distal movable barrel labelled 805 is aligned with the stationary barrel 855. An axial bore 807 runs therethrough. The distal portion of the bore 807 is enlarged and is threaded for threadably connecting with the threaded end 675 of the hollow shaft 655. At the inner terminus of the threaded portion of the bore, there is an annular shelf 809 or projection resulting from the remainder of the bore 807 being reduced in diameter relative to the threaded portion of the bore. The remainder of the bore is smooth and is slightly smaller than the outside diameter of the hollow shaft 655. An annular sealing ring 810 is located in the bore and abuts against the annular shelf 809. The stop ring centers and limits movement of the inner shaft 670.

The cylinder-shaped cartridge 862 will now be discussed in greater detail. The cartridge is about 1.75 inches in length. It is axially positioned in the stationary barrel 855 and the movable barrel 805. The cartridge has an axial bore running therethrough. The diameter is sufficient to allow the proximal cylindrical portion 674 and the ball end of the inner shaft to pass through. However, the axial bore of the cartridge prevents the larger cylindrical portion 673 from passing through. The distal portion of the cartridge mates with the bore 807 in the movable barrel 805. The proximal annular ridge 866 on the cartridge mates against the larger bore opening 859 in the proximal end of the stationary barrel 855. This prevents the remainder of the cartridge from penetrating any further into the stationary barrel 855 or beyond that point. The ridge 866 and the larger bore 859 act as a stop. The proximal end of the cartridge 862 has a nipple 865. The nipple has a Orlon cylindrical ring 762 secured to it. The Orlon ring has an axial bore. The inner shaft 674 passes through the cartridge 862, and also through the Orlon ring 674. The Orlon ring functions as a pneumatic seal to minimize the leakage of carbon dioxide gas from the inner shaft when the instrument is in use. The Torlon ring 762 also functions as a bushing. The distal end of the cartridge has a small transverse radial hole 867 drilled through the cartridge wall. The movable barrel 805 also has a complementary radial hole 801. After the barrel and clutch means are assembled on the instrument, a small set screw 803 or rivet is placed in both holes 867 and 801. This keeps the assembly locked together.

The circumference of the thumb wheel 755 is shaped like a star with circular indentations formed between the points of the star. The star surface is designed for easy gripping by the surgeon while he is wearing latex gloves while performing an operation. The points of the star form a series of nubs. The Thumb wheel has three stepped bores 756, 757, and 758. All are in axial alignment. The smallest bore 758 is located proximally in the thumb wheel. It is the same diameter as the outside diameter of the ring 863. The second larger bore 757 is the same diameter as a coil spring 760 placed in the thumb wheel 755. The transition point where the smaller bore meets the medium bore forms an annular seat where the distal end of the coil spring 760 can abut against. The large bore mates with the flange 825 on the movable barrel 805. The surface of the large bore has a radial projection 770 or key that mates with the longitudinal surface groove or keyway 822 cut into both the flange and outside surface of the movable barrel 805. These two complementary parts force the movable barrel 805 and thumb wheel 755 to rotate in unison, and also act as a guideway to allow the thumb wheel to slide back and forth within a limited range on the movable barrel. The annular shelf formed where the bores 757 and 758 meet on the thumb wheel acts as a seat for the proximal end of the coil spring 760. The coil spring fits over the outside cylinder portion of the movable barrel proximal to the flange 825. The coil spring has a diameter slightly smaller than the diameter of the medium bore 757 in the thumb wheel. The coil spring occupies the space between the medium bore in the thumb wheel and the proximal cylinder portion on the movable barrel 805. After the components forming the barrel and clutch means are assembled, the coil spring is compressed and is under constant tension. It causes the thumb wheel 755 to be continuously biased against the distal face of the stationary barrel 855. As previously stated, the distal face of the stationary barrel has a circumferential array of radial teeth 861 cut into the face. The distal end of the thumb wheel also a face with a circumferential array of radial teeth 775 cut into its face. Both sets of teeth are complementary and mesh together like gears. The biasing of the coil spring 760 forces both sets of teeth 775 and 864 to continuously mesh together to effectively lock the thumb wheel to the stationary barrel. This in turn prevents the inner shaft from rotating. The cutting tips 700 extending from the distal end of the inner shaft cannot change their angular orientation unless the inner shaft is rotated. The thumb wheel and the associated parts function like a clutch to allow the inner shaft to rotate to allow the surgeon to change the orientation of the cutting tips. By simply turning the thumb wheel a few degrees at a time, the angular orientation of the cutting tips are change the same number of degrees. The spacing of the teeth 775 and 864 determines the minimum angular change. However, the spacing of the teeth is sufficiently small so that the increments are very small. If the surgeon rotates the thumb wheel 755 a quarter of a turn the angular orientation of the tips are changed ninety degrees. If the surgeon rotates the thumb wheel one-half of a turn, the angular orientation of the cutting tips is changed 180 degrees. Since the thumb wheel can rotate clockwise or counterclockwise, the surgeon need only turn the thumb wheel a half a turn at most to set the angle of the tips at any desired angle. While turning the thumb wheel, the facing teeth 775 on the thumb wheel move away from the teeth 864 on the stationary barrel until another tooth depression is reached. The teeth are formed by very small V-shaped cuts in the face. The facing teeth ride up on each other to the crest of the tooth then fall back together after passing the crest. The spaces between the teeth are referred to as lands. The teeth mesh by having the crest on one face mating with the land on the other face. The movement between the lands and the crests causes a clicking sound. This audible clicking sound helps the surgeon to judge how far to turn the thumb wheel. After using the instrument for some time, the surgeon can judge the angular change by associating it with the number of clicks. The coil spring forces the thumb wheel against the stationary barrel to make a clicking noise as the thumb wheel is rotated.

The pair of handles will now be discussed in greater detail. The pair of handles are labelled 600 and 620. The proximal handle 600 has a finger ring 605 at its bottom and an integral socket 900 at its top. As previously discussed, the socket locks and holds the end of the movable shaft. About two thirds up from the base, the handle makes a bent angle proximally of about ninety degrees from the rest of shank of the handle. The bent portion is labeled 630. The area of the bend is enlarged to strengthen the rigidity of the handle and to form an area where the two handles can be pivotally secured with a set screw 606. The proximal handle forms a mirror image with the distal handle up to the area where the two are pivotally connected with one another. All the drawings illustrate both handles in an open position. If one were to squeeze both handles together so that they touch one another, the mirror image relationship is readily observed. The upper portion 623 has a brace for pivotally securing the stationary barrel. After the instrument is assembled as shown in FIG. 14 the distal handle is vertical relative to the hollow shaft. The proximal handle, is angled away from the shaft combination. This angled combination is very important to the present invention. When the surgeon squeezes the pair of handles to cut a piece of tissue the position of the end or tip of the instrument remains stationary for the surgeon. The base of the cutting tips retract into the hollow tube forcing the cutting blades to close like a pair of scissors to cut the tissue. The blades move, but not the stationary tip. Because the laparoscopic procedure is being done inside the patient, the surgeon cannot actually see what he is cutting with the instrument- He must rely on the images formed on the television monitor that are relayed from a light tube or miniature camera in the patient. Because the instrument does not move during the cutting process, the images relayed to the surgeon do not require realignment to the image receiver to the tip of the present invention.

Obviously, many modifications and variants of the present invention are possible in light of the above teachings. It is therefore to be understood that the full scope of the invention is not limited to the details disclosed herein, but may be practiced otherwise than as specifically described.

What is claimed is:

1. A surgical instrument, which comprises:
   a rotatable combination shaft having a proximal end and a distal end;
      said rotatable shaft combination comprising:
      an outer hollow shaft;
      an inner shaft slidably positioned axially in said outer hollow shaft;
      means at said distal end of said inner shaft for cutting;
      anchor means at said proximal end of said inner shaft;
   a pair of distal and proximal squeeze handles pivotally secured together;
   mounting means on each of said handles;
   means attached to said mounting means on said proximal handle for releasably securing said anchor means at said proximal end of said inner shaft;
   stationary barrel means having a proximal end and a distal end, and having an axial bore and mounted on said mounting means of said distal handle;
   movable barrel means having an axial bore and mounted at said distal end of said stationary barrel means;
   means for engaging said shaft combination with said removable barrel means so that both can rotate in unison;
   clutch means for allowing said shaft combination and said rotatable barrel means to temporarily disengage from said stationary barrel means to allow angular adjustment of said means for cutting on said shaft combination; and
   cartridge means positioned in said axial bore of said movable barrel and said axial bore of said stationary barrel means for holding said movable barrel means, said shaft combination, said stationary barrel means and said clutch means together as a unit;
   said cartridge means having an axial bore for allowing said inner shaft to reciprocate therein.

2. The surgical instrument as recited in claim 1 wherein said means attached to said mounting means on said proximal handle for releasably securing said anchor means at said proximal end of said shaft includes a socket with a quick-release button.

3. The surgical instrument as recited in claim 2 wherein said anchor means at said proximal end of said shaft includes a ball-like tip so that said socket will secure said tip and yet allow said inner shaft to rotate and reciprocate when desired, and allows said inner shaft to be removed by pressing said quick-release button and pulling said inner shaft out from said outer shaft.

4. The surgical instrument as recited in claim 1 wherein said mounting means on each of said handles includes a yoke and a brace.

5. The surgical instrument as recited in claim 1 wherein said pair of distal and proximal squeeze handles pivotally secured together include angled shanks and braces so that when said pair of handles are squeezed together by the surgeon during the operation, said socket is pulled proximally relative to said stationary hollow shaft whereby said hollow shaft and supports remain stationary while said means for cutting at said proximal end of said inner shaft are cutting tissue.

6. The surgical instrument as recited in claim 1 wherein said means at said distal end of said inner shaft for cutting includes a pair of opposed scissor-like blades, each said blade being secured to said proximal end of said inner shaft with a flexible arm angled outwardly from the axis of said shaft combination, said blades and flexible arms flexing together in response to the surgeon squeezing said pair of handles in order to cut tissue positioned between said pair of blades.

7. The surgical instrument as recited in claim 1 wherein said inner shaft can be removed from said instrument and replaced with another shaft.

8. The surgical instrument as recited in claim 1 wherein said inner shaft and said means for cutting can be rotated about its axis by actuating and turning said clutch means.

9. A surgical instrument, which comprises:

a rotatable combination shaft having a proximal end and a distal end;
said rotatable shaft combination comprising:
an outer hollow shaft;
an inner shaft;
means at said distal end of said inner shaft for cutting;
anchor means at said proximal end of said inner shaft;
a pair of distal and proximal squeeze handles pivotally secured together;
locking means on said handles for keeping said handles closed unless a release means is disengaged;
mounting means on each of said handles;
means attached to said mounting means on said proximal handle for releasably securing said anchor means to said proximal end of said inner shaft;
stationary barrel means having a proximal end and a distal end, and having an axial bore, and mounted on said mounting means of said distal handle;
gear teeth means on said proximal end of said stationary barrel means forming a ring of gear teeth;
movable barrel means mounted at said distal end of said stationary barrel means;
means for engaging said shaft combination with said movable barrel means so that both can rotate in unison;
thumb wheel means having a distal face and a proximal face and mounted on said inner shaft and distal to said stationary barrel;
a ring of gear teeth means on said distal face of said thumb wheel means for complementary mating with said gear teeth means on said stationary barrel means;
clutch means for allowing said shaft combination and rotatable barrel means to temporarily disengage from said stationary barrel means to allow angular adjustment of said means for cutting on said shaft combination;
cartridge means positioned in said axial bore of said movable barrel and said axial bore of said stationary barrel for holding said movable barrel, said shaft combination, said stationary barrel and said clutch means together as a unit;
said cartridge means having an axial bore for allowing said inner shaft to reciprocate therein.

10. The surgical instrument as recited in claim 9 wherein said means attached to said mounting means on said proximal handle for releasably securing said anchor means at said proximal end of said shaft includes a socket with a quick-release button.

11. The surgical instrument as recited in claim 10 wherein said anchor means at said proximal end of said shaft includes a ball-like tip so that said socket will secure said tip and yet allow said inner shaft to rotate and reciprocate when desired, and allow said inner shaft to be removed by pressing said quick-release button and pulling said inner shaft out from said outer shaft.

12. The surgical instrument as recited in claim 9 wherein said mounting means on each of said handles includes a yoke and a brace.

13. The surgical instrument as recited in claim 9 wherein said pair of distal and proximal squeeze handles pivotally secured together include angled shanks and braces so that when said pair of handles are squeezed together by the surgeon during the operation, said socket is pulled proximally relative to said stationary hollow shaft whereby said hollow shaft and supports remain stationary while said cutting means at said proximal end of said inner shaft are cutting tissue.

14. The surgical instrument as recited in claim 9 wherein said means at said distal end of said inner shaft for cutting includes a pair of opposed scissor-like blades, each said blade being secured to said proximal end of said inner shaft with a flexible arm angled outwardly from the axis of said shaft combination, said blades and flexible arms flexing together in response to the surgeon squeezing said pair of handles in order to cut tissue positioned between said pair of blades.

15. The surgical instrument as recited in claim 9 wherein said inner shaft can be removed from said instrument and replaced with another shaft.

16. The surgical instrument as recited in claim 9 wherein said inner shaft and said means for cutting can be rotated about its axis.

17. A monopolar laparoscopic electrocautery laparoscopic surgical instrument, which comprises:
a rotatable combination shaft having a proximal end and a distal end;
said rotatable shaft combination comprising:
an outer hollow shaft;
an inner shaft slidably positioned axially in said outer hollow shaft;
means at said sital end of said inner shaft for cutting;
anchor means at said proximal end of said inner shaft;
a pair of distal and proximal squeeze handles pivotally secured together;
means on said handles and said instrument for receiving an electric cored and transmitting electric current to said means for cutting on said distal end of said inner shaft;
mounting means on each of said handles;
means attached to said mounting means on said proximal handle for releasably securing said anchor means at said proximal end of said inner shaft;
stationary barrel means having a proximal end and a distal end, and having an axial bore and mounting on said mounting means of said distal handle;
movable barrel means having an axial bore and mounted at said distal end of said stationary barrel means;
means for engaging said shaft combination with said movable barrel means so that both can rotate in unison;
clutch means for allowing said shaft combination and said rotatable barrel means to temporarily is engage from said stationary barrel means to allow angular adjustment of said means for cutting on said shaft combination;
cartridge means postioned in said axial bore of said movable barrel and said axial bore of said stationary barrel for holding said movable barrel, said shaft combination, said stationary barrel and said clutch means together as a unit;
said cartridge means having an axial bore for allowing said inner shaft to reciprocate therein; and
electric insulation means covering the exterior of said instrument for protection against electric shock whenever electric current is passed through said instrument.

18. The surgical instrument as recited in claim 17 wherein said means attached to said mounting means on said proximal handle for releasably securing said anchor means at said proximal end of said shaft includes a socket with a quick-release button.

19. The surgical instrument as recited in claim 18 wherein said anchor means at said proximal end of said shaft includes a ball-like tip so that said socket will secure said tip and yet allow said inner shaft to rotate and reciprocate when desired, and allow said inner shaft to be removed by pressing said quick-release button and pulling said inner shaft out from said outer shaft.

20. The surgical instrument as recited in claim 17 wherein said mounting means on each of said handles includes a yoke and a brace.

21. The surgical instrument as recited in claim 17 wherein said pair of distal and proximal squeeze handles pivotally secured together include angled shanks and braces so that when said pair of handles are squeezed together by the surgeon during the operation, said socket is pulled proximally relative to said stationary hollow shaft whereby said hollow shaft and supports remain stationary while said cutting at said proximal end of said inner shaft are cutting tissue.

22. The surgical instrument as recited in claim 17 wherein said means at said distal end of said inner shaft for cutting includes a pair of opposed scissor-like blades each said blade being secured to said proximal end of said inner shaft with a flexible arm angled outwardly from the axis of said shaft combination, said blades and flexible arms flexing together in response to the surgeon squeezing said pair of handles in order to cut tissue positioned between said pair of blades.

23. The surgical instrument as recited in claim 17 wherein said inner shaft can be removed from said instrument and replaced with another shaft.

24. The surgical instrument as recited in claim 17 wherein said inner shaft and said means for cutting can be rotated about its axis.

* * * * *